US008481720B2

(12) United States Patent
Kim et al.

(10) Patent No.: US 8,481,720 B2
(45) Date of Patent: Jul. 9, 2013

(54) MANUFACTURING METHOD OF TAGATOSE USING GALACTOSE ISOMERIZATION OF HIGH YIELD

(75) Inventors: Seong-bo Kim, Seoul (KR); Seung-won Park, Gyeonggi-do (KR); Sang-hoon Song, Gyeonggi-do (KR); Kang-pyo Lee, Seoul (KR); Deok-kun Oh, Gyeonggi-do (KR); Byoung-chul Lim, Gyeonggi-do (KR); Hye-jung Kim, Seoul (KR)

(73) Assignee: CJ Cheiljedang Corporation, Seoul (KR)

( * ) Notice: Subject to any disclaimer, the term of this patent is extended or adjusted under 35 U.S.C. 154(b) by 652 days.

(21) Appl. No.: 12/513,866

(22) PCT Filed: Dec. 10, 2007

(86) PCT No.: PCT/KR2007/006389
§ 371 (c)(1), (2), (4) Date: Jul. 20, 2009

(87) PCT Pub. No.: WO2008/072864
PCT Pub. Date: Jun. 19, 2008

(65) Prior Publication Data
US 2009/0306366 A1 Dec. 10, 2009

(30) Foreign Application Priority Data
Dec. 11, 2006 (KR) ........................ 10-2006-0125594

(51) Int. Cl.
*C07H 3/02* (2006.01)
(52) U.S. Cl.
USPC ........................................................ 536/125
(58) Field of Classification Search
None
See application file for complete search history.

(56) References Cited

U.S. PATENT DOCUMENTS

| | | | |
|---|---|---|---|
| 3,894,913 | A | 7/1975 | Watanabe et al. |
| 3,957,578 | A | 5/1976 | Narita et al. |
| 4,273,922 | A | 6/1981 | Hicks |
| 4,663,449 | A | 5/1987 | Barker et al. |
| 5,002,612 | A | 3/1991 | Beadle et al. |
| 5,078,796 | A | 1/1992 | Beadle et al. |
| 6,057,135 | A | 5/2000 | Ibrahim et al. |
| 6,797,309 | B2 | 9/2004 | Monagle |
| 2003/0175909 | A1* | 9/2003 | Kim et al. ............... 435/94 |
| 2005/0161401 | A1 | 7/2005 | Heikkila et al. |
| 2009/0004642 | A1 | 1/2009 | Magaletta et al. |
| 2010/0285539 | A1 | 11/2010 | Kim et al. |

FOREIGN PATENT DOCUMENTS

| | | |
|---|---|---|
| EP | 0375046 | 6/1990 |
| JP | 54-12538 | 5/1979 |
| KR | 1020010090004 A | 10/2001 |
| KR | 1020020051835 A | 6/2002 |
| KR | 1020060068505 A | 6/2006 |
| KR | 10-2006-0120197 | 11/2006 |
| WO | WO 02-15712 A2 | 2/2002 |
| WO | 2005/047510 | 5/2005 |
| WO | WO 2006/058092 | 6/2006 |

OTHER PUBLICATIONS

Lim, B.-C. et al., Biological Society of Korea Conference, 2007 Conference and International Symposium, Apr. 2007, pp. 25-25, Korea Society for Biotechnology (with English translation of publication date); also available at http://www.earticle.net/Article.aspx?sn=99490; last accessed Apr. 24, 2012.*
Lim, Byung-Chul et al., Biotechnology Progress, "High Production of D-Tagatose by the Addition of Boric Acid", 2007, vol. 23, pp. 824-828.*
Ekeberg et al. (2002) Carbohydrate Research 337:779-786, "Base catalysed isomerisation of aldoses of the *arabino* and *lyxo* series in the presence of aluminate".
Kim and Oh. (2005) J. Biotech. 120(2):162-73, "Purification and characterization of an L-arabinose isomerase from an isolated strain of *Geobacillus thermodenitrificans* producing D-tagatose".
Lee et al. (Mar. 2004) Appl. Environ. Microbiol. 70:1397-1404, "Characterization of a Thermostable L-Arabinose (D-Galactose) Isomerase from the Hyperthermophilic Eubacterium *Thermotoga maritime*".
Oh et al. (2001) Biotechnology Lett. 23, 1859-1862, "Development of an immobilization method of L-arabinose isomerase for industrial production of tagatose".
Tkac et al. (1999) Biotechnology Techniques 13:931-936, "Rapid and sensitive galactose oxidase-peroxide biosensor for galactose detection with prolonged stability".
Yoon et al. (2003) World J. of Microbiology & Biotechnology, 19:47-51, "Properties of L-arabinose isomerase from *Escherichia coli* as biocatalyst for tagatose production".
Search Report dated Mar. 10, 2008; PCT/KR2007/006389.
Written Opinion dated Mar. 10, 2008; PCT/KR2007/006389.
U.S. Appl. No. 12/812,567, filed Jul. 12, 2010, Kim et al.
Green et al. (1956) Journal of Biological Chemistry, 219:557-568, "Enzymatic Conversion of L-Fucose to L-Fuculose".
Cohen (1953) Journal of Biological Chemistry, 201:71-84, "Studies on D-Ribulose and its Enzymatic Conversion to D-Arabinose".
Mitsuhashi et al. (1953) Journal of Biological Chemistry 204:1011-1018, "Conversion of D-Xylose to D-Xylulose in Extracts of *Lactobacillus pentosus*".
EP Search Report issued Oct. 29, 2012 in EP 09705280.7.

* cited by examiner

*Primary Examiner* — Shaojia Anna Jiang
*Assistant Examiner* — Bahar Craigo
(74) *Attorney, Agent, or Firm* — Swanson & Bratschun, L.L.C.

(57) ABSTRACT

The present invention relates to a manufacturing method of tagatose using galactose isomerization of high yield, more particularly a method to enhance conversion rate of isomerization by adding borate which binds specifically to tagatose and a manufacturing method of tagatose using the same.

2 Claims, 5 Drawing Sheets

MANUFACTURING METHOD OF TAGATOSE USING GALACTOSE ISOMERIZATION OF HIGH YIELD

RELATED APPLICATIONS

This application is a 35 U.S.C. §371 national phase application of PCT/KR2007/006389 (WO 2008/072864), filed on Dec. 10, 2007, entitled "Manufacturing Method Of Tagatose Using Galactose Isomerization of High Yield," which application claims the benefit of Korean Patent Application Serial No. 10-2006-0125594, filed on Dec. 11, 2006. Each of these applications is specifically incorporated herein by reference in its entirety.

TECHNICAL FIELD

The present invention relates to a manufacturing method of tagatose using galactose isomerization of high yield, more particularly a method to enhance conversion rate of isomerization dramatically by adding borate which binds specifically to tagatose, the ketose, into the reaction solution under the optimum condition and a manufacturing method of tagatose with high yield using the same.

BACKGROUND ART

Up to date, tagatose has been prepared from galactose by chemical synthesis. According to the conventional method of chemical synthesis, galactose is isomerized in the presence of inorganic salt, mediated by metal hydroxide as a catalyst, to form the intermediate of the metal hydroxide-tagatose complex. The intermediate is neutralized by acid to produce tagatose. However, this conventional method of chemical synthesis is very complicated in its process and inefficient and generates industrial wastes, even if it might be economical and give the product with high yield.

Another method to produce tagatose is an enzyme mediated conversion, in which aldose or aldose derivatives are converted into ketose or ketose derivatives, followed by the conversion of galactose into tagatose using the enzyme. It is known that arabinose isomerase that has been used for the conversion of L-arabinose into L-ribulose can generate tagatose by using galactose as a substrate in vitro. Accordingly, many arabinose isomerases having different origins and manufacturing methods of tagatose from galactose using the same have been reported.

Isomerization of galactose to tagatose is a kind of reversible reaction, suggesting that the concentration of the reactant is balanced with the concentration of the product. This enzyme reaction is characterized by that the conversion rate relatively increases in proportion to the reaction temperature thermodynamically. Therefore, development of a novel enzyme stable at high temperature and the process of isomerization using the same are key factors for the enzyme mediated conversion using isomerase to produce tagatose.

The conventional arabinose isomerase originated from *E. coli* exhibited very low tagatose conversion rate from galactose, which was 25%, when the isomerization was carried out at 30° C. for 24 hours. Arabinose isomerase originated from the thermophilic microorganism *Geobacillus stearothermophilus* exhibited 46% of conversion rate at 60° C. which is a stable reaction condition have been reported. When hyperthermophilic arabinose isomerase originated from *Thermotoga maritima* was used for the isomerization reaction at 70° C. and 80° C., the conversion rate from galactose to tagatose was 50% and 56%, respectively (Oh, D. K., Kim, H. J., Ryu, S. A., Kim, P., 2001. Development of an immobilization method of I-arabinose isomerase for industrial production of tagatose. Biotechnol. Lett. 23, 1859-1862; Kim, H. J., Oh, D. K., 2005. Purification and characterization of an L-arabinose isomerase from an isolated strain of *Geobacillus thermodenitrificans* producing d-tagatose, J. Biotech. Nov 4; 120(2):162-73. Epub 2005 Aug. 9; Lee, D. W., Jang, H. J., Choe, E. A., Kim, B. C., Lee, S. J., Kim, S. B., Hong, Y. H., Pyun, Y. R., 2004. Characterization of a thermostable I-arabinose (d-galactose) isomerase from the hyperthermophilic eubacterium *Thermotoga maritima*. Appl. Environ. Microbiol. 70, 1397-1404.).

The application of thermophilic enzyme and the reaction at high temperature can increase the conversion rate from galactose to tagatose gradually. However, in general, browning of sugar solution at reaction temperature of 70° C. or up is dramatically increase in proportion to the temperature rise. In addition, the byproducts generated by such high temperature reaction have a bad influence on the purity of the final product and purification costs. Therefore, the reaction temperature rise is limited. So, the best applicable reaction temperature seems to be 70° C. and the maximum conversion rate of isomerization at that temperature is 56%. The higher conversion rate has not been obtained, so far.

DISCLOSURE OF THE INVENTION

Thus, the present inventors completed this invention by confirming that the manufacturing method of tagatose using galactose isomerization which includes the step of adding borate specifically binding to tagatose gives higher yield than the conventional method.

It is an object of the present invention to provide a manufacturing method of tagatose by galactose isomerization using a thermophilic isomerase and host cells containing the same, more particularly a method to enhance conversion rate of the isomerization by adding borate which binds specifically to tagatose and a manufacturing method of tagatose with high yield using the same.

It is another object of the present invention to provide a method to artificially enhance conversion rate of the isomerization by adding a proper amount of borate and performing the isomerization at high temperature under the condition which induce selective binding of the borate to tagatose.

To achieve the above objects, the present inventors increased the conversion rate dramatically by adding borate binding specifically to tagatose to produce tagatose from galactose by using arabinose isomerase originated from thermophilic or hyperthormophilic microorganism, and further confirmed that tagatose could be efficiently produced from galactose by using the method with high yield.

The present invention is described in detail hereinafter.

The arabinose isomerase herein can be originated from various thermophilic microorganisms including *Geobacillus* sp., *Thermotoga* sp., *Thermus* sp. microorganisms, etc, but not always limited thereto. The arabinose isomerases originated from different strains can be applied in different reaction conditions as long as the conditions are within the optimum reaction conditions of their own (temperature, pH). So, every isomerization performed under such conditions is included in the criteria of the invention.

The salt that is able to bind specifically to tagatose herein is borate. The borate used in the present invention was rather specifically bound to tagatose than galactose (FIG. 1). The addition of borate induces the much more effective galactose isomerization than the conventional method without using borate, and as a result the phase equilibrium between substrate and reactant is transferred.

The effect of a salt of the invention is not limited to borate and any other salts binding specifically to tagatose can be used, that is the effect of the invention can be caused by different salts under the different conditions. Therefore, all the mechanisms of adding tagatose specific salt to increase conversion rate are included in the criteria of the present invention.

BRIEF DESCRIPTION OF THE DRAWINGS

The application of the preferred embodiments of the present invention is best understood with reference to the accompanying drawings, wherein.

BEST MODE FOR CARRYING OUT THE INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLES

Example 1

Binding Capacity of Borate to Substrate and Product

Figure 1:
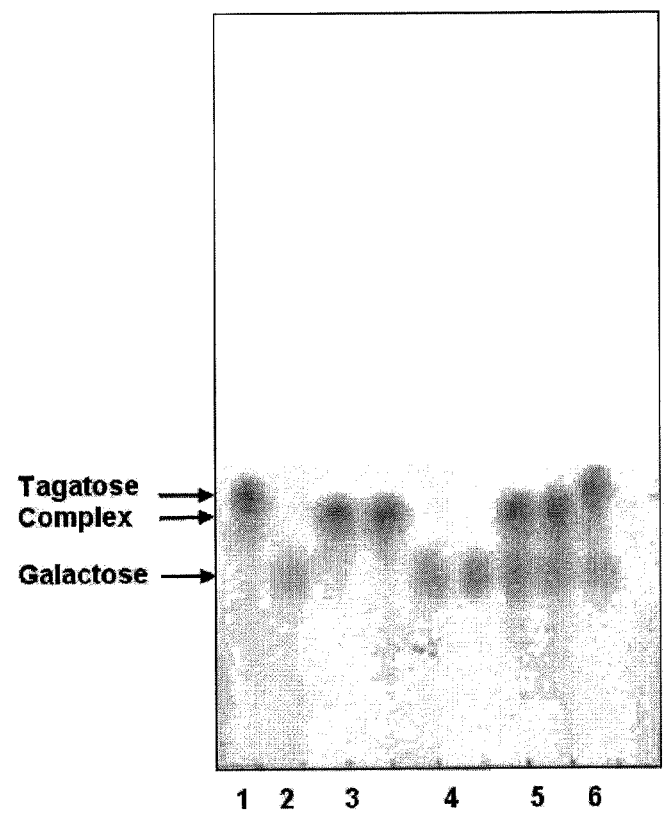
FIG. 1 is a diagram illustrating the results of TLC (thin layer chromatography) performed after the reaction of galactose and tagatose with borate under the various conditions.
Lane 1, tagatose
Lane 2, galactose
Lane 3, galactose+borate
Lane 4, tagatose+galactose+borate
Lane 5, tagatose+galactose

To investigate the interaction of the two sugar sources, galactose and tagatose, presence in the product of isomerization with borate, each sugar source was added into borate buffer, followed by comparison. Galactose, tagatose and the mixture thereof (1:1) were prepared by 100 mM each. 1 ml of the sugar source was mixed with 1 ml of 100 mM borate buffer (pH 9.5), which stood at room temperature for 30 minutes and then proceeded to TLC (thin layer chromatography). 50 μl of each reaction product was loaded on TLC plate, which was dried and developed in 85% acetonitrile solution. Color development was performed to analyze the result and at this time the coloring agent was prepared with 95% methane, 5% sulfuric acid and 0.3% N-1-naphthylethylenediamine. As a result, borate was bound specifically to tagatose, and this result is shown in FIG. 1.

Example 2

Expression of Thermophilic Arabinose Isomerase

To perform galactose isomerization to produce tagatose from galactose at high temperature, arabinose isomerase gene originated from the thermophilic microorganism *Geobacillus thermodenitrificans* was used. Based on the previous data, the mutant gene in which $450^{th}$ (cystein) and $475^{th}$ (asparagine) amino acids are replaced with serine and lysine was inserted into the vector pTrc99A, which was introduced into *Escherichia coli* BL21 (DE3, Invitrogen, U.S.A.) for transfection. The transformant was used as a producing strain. The recombinant strain was inoculated in LB medium (Bacto-tryptone 10 g/L, yeast extract 5 g/L, NaCl 10 g/L) containing 50 μg/ml of ampicillin at the primary concentration of $OD_{600}$=0.1, followed by culture at 37° C. for 2 hours. Then, enzyme expression was induced by adding IPTG (Isopropyl-beta-D-thiogalactosidase) at the final concentration of 1 mM. To measure the enzyme activity of the expressed arabinose isomerase, the cells were recovered by centrifugation with the culture solution at 8,000×g for 10 minutes. The cells were resuspended in 50 mM Tris-HCL buffer (pH 7.0), and lysed by sonification. The lysate was used as a crude enzyme solution to measure the galactose isomerization. The galactose isomerization activity was measured with the mixture of 100 μl of the enzyme solution containing 40 mM of galactose as a substrate and 1 ml of reaction buffer (50 mM Tris-HCl, pH 7.0). At that time, $MnCl_2$ (final conc.: 5 mM) and $MgCl_2$ (final conc.: 1 mM) were also added in the reaction solution.

Example 3

Optimization of the Enzyme Reaction Conditions

Figure 2:
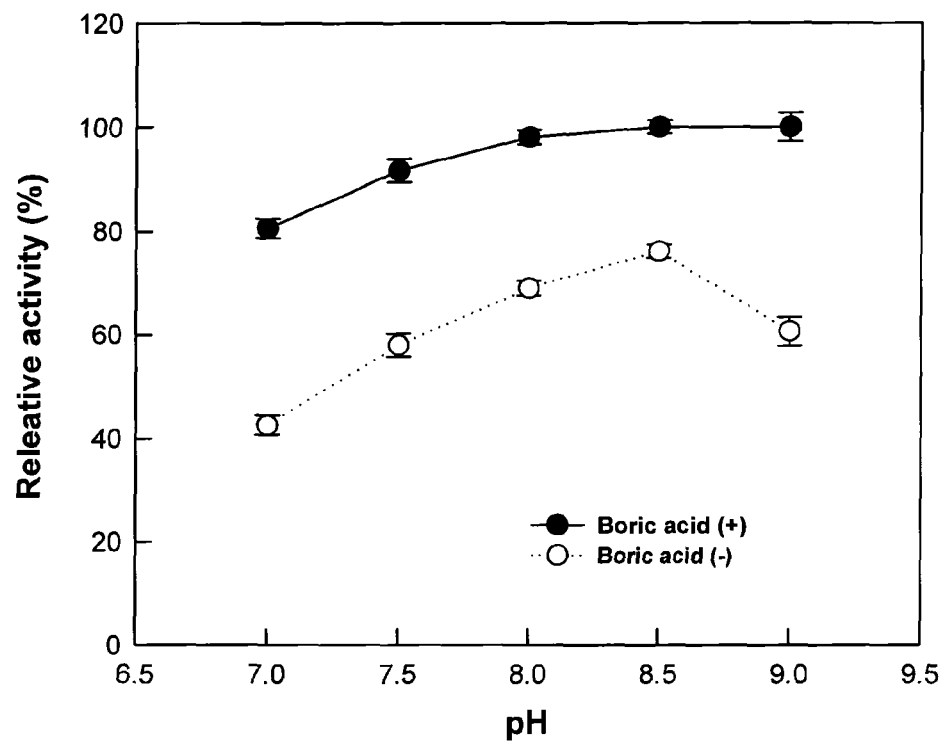
FIG. 2 is a graph illustrating the pH dependent conversion rate of galactose to tagatose with and without the addition of borate, in which the highest conversion rate was considered as 100 and the relative values were calculated. ● indicates the result of the reaction in the presence of 20 mM of borate, and ○ indicates the result of the reaction in the absence of borate.

To determine optimum pH for the enzyme reaction in the presence of borate, the reaction substrate solutions were prepared by mixing galactose and borate buffers having different pH (pH 7.0, 7.5, 8.0, 8.5, 9.0). The final composition of the reaction substrate stock solution was balanced with 100 mM of galactose and 20 mM of borate. The purified enzyme was added into the reaction substrate solution (4 mg/ml), followed by reaction at 60° C. until it reached equilibrium. The conversion rate of the substrate reached equilibrium was analyzed and compared with relative value (FIG. 2).

Figure 3:
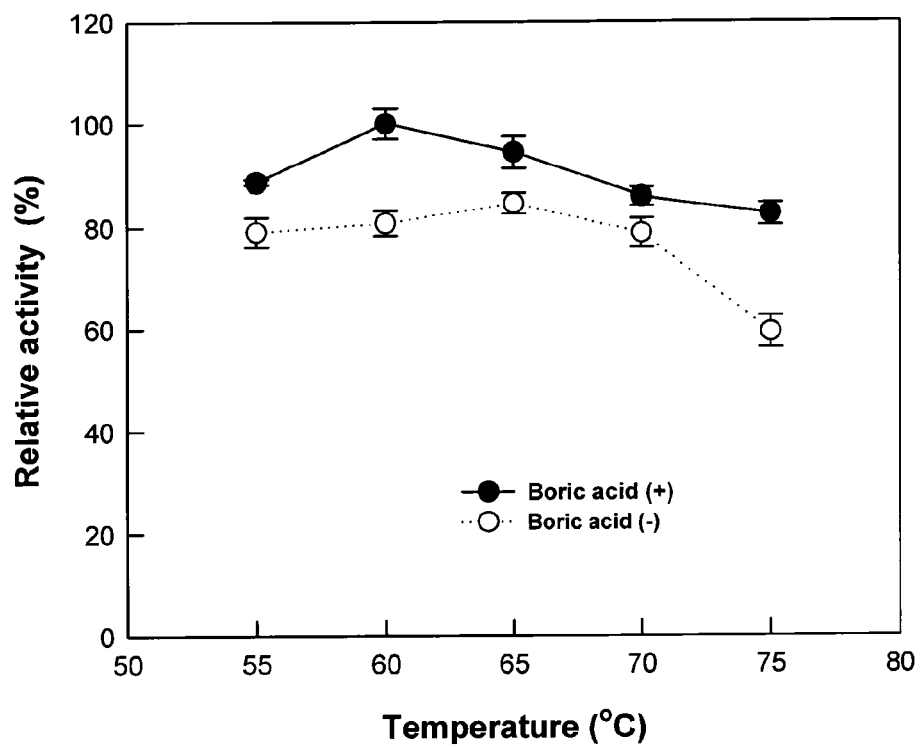
FIG. 3 is a graph illustrating the temperature dependent conversion rate of galactose to tagatose with and without the addition of borate, in which the highest conversion rate was considered as 100 and relative values were calculated. ● indicates the result of the reaction in the presence of 20 mM of borate, and ○ indicates the result of the reaction in the absence of borate.

As a result, the conversion rate of galactose to tagatose was increased by the addition of borate. The conversion rate was gradually increased under alkali condition of neutral pH to pH 8.0 and then it was regular at pH 8.5 or up. In general, chemical synthesis is dominant over enzymatic production under the condition of pH 9.0 or up. So, pH 8.5 at which the enzyme activity was the highest and the conversion rate was best increased was determined as optimum pH for the reaction. 4 mg/ml of crude enzyme solution was added into the optimum reaction substrate (100 mM galactose, 20 mM borate, pH 8.5). The conversion rate was measured according to the reaction temperature. The relative values were obtained by considering the point where tagatose was produced in largest quantity as 100 (FIG. 3).

As a result, the highest conversion rate was obtained when borate was added at 60° C.

Example 4

Figure 4:
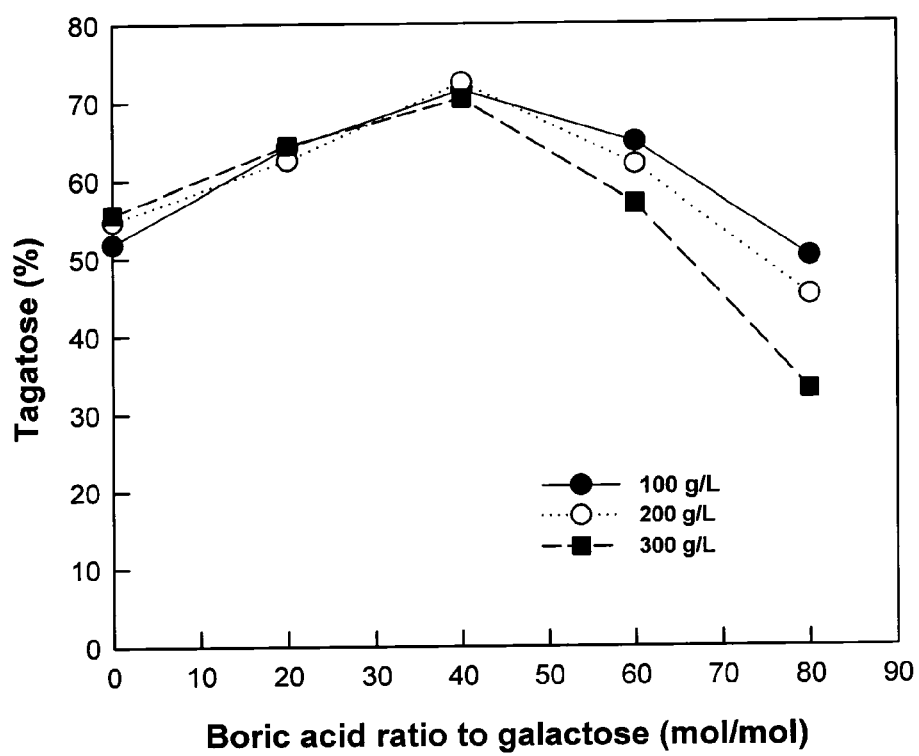
FIG. 4 is a graph illustrating the conversion rates according to the different conditions, in which borate is added at different molar ratios to high concentrated substrates (10 g/L, 200 g/L and 300 g/L).

Optimization of Conversion Rate from the High Concentrated Substrate According to the Molar Ratio of Borate To investigate whether the conversion rate of galactose to tagatose was increased by the addition of borate to the substrate of high concentration and to optimize the conditions for the reaction, galactose substrate solutions were prepared at different concentrations (100 g/L, 200 g/L and 300 g/L). The molar ratio of galactose to borate in each substrate solution was respectively 100:20, 100:40, 100:60 and 100:80, and the reaction was performed equally at 60° C. under pH 8.5 (FIG. 4).

As a result, it was confirmed that the action of borate in the galactose isomerization to tagatose was not related to the concentration of substrate, galactose, and the conversion rate was increased in proportion to the increase of the molar ratio of borate. The optimum molar ratio of galactose to borate was confirmed to be 100:40.

Example 5

Production of Tagatose Under the Optimum Reaction Condition

Figure 5:
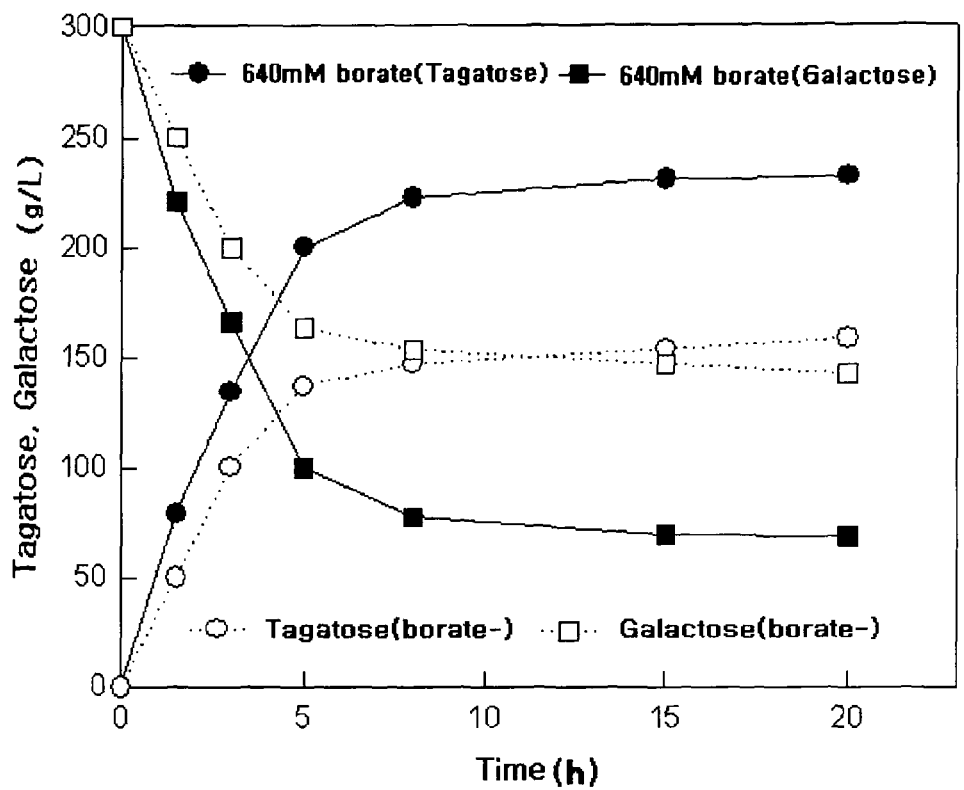
FIG. 5 is a graph illustrating the results of isomerization reaction to produce tagatose performed in substrate solution containing 300 g/L of galactose (substrate:borate=100:40, molar ratio) in the presence and absence of borate. ┼ indicates the result of the reaction in the presence of 640 mM of borate, and ○ indicates the result of the reaction in the absence of borate. ■ and □ L indicate the consumed galactose and the generated tagatose respectively.

The result of the experiment performed with the addition of borate at the molar ratio optimized in examples 1~4 was compared with the result of the experiment performed without borate. More particularly, the substrate solution comprising 300 g/L of galactose and 640 mM of borate (pH 8.5) was prepared, to which 30 mg/ml of the crude enzyme solution was added, followed by isomerization at 60° C. (FIG. 5).

With the addition of borate, the conversion rate was increased dramatically. It was confirmed that the tagatose yield given from the galactose substrate of 300 g/L after 20 hours of reaction was 158 g/L when borate was not added and 232 g/L when borate was added, indicating that the conversion rate of each group was 52.7% and 77.3% respectively.

Industrial Applicability

As explained hereinbefore, when borate was selectively added to galactose isomerization to produce tagatose mediated by arabinose isomerase without affecting the optimum enzyme reaction condition, the conversion rate was significantly increased. The conversion rate of isomerization increases according to the increase of temperature thermodynamically. Thus, application of high-temperature reaction can increase the conversion rate from galactose to tagatose. However, in general, the treatment process of sugar have trouble in the reaction at 60° C. to 70° C. or up because of the characteristics of sugar which turns brown so easily at the high temperature. Therefore, the substantially possible conversion rate of galactose to tagatose using arabinose isomerase in the present invention was 55% at 70° C. However, according to the method of the present invention characterized by the addition of borate, the conversion rate under the same condition can be dramatically increased with reducing production costs.

The invention claimed is:

1. An enzymatic isomerization method of manufacturing tagatose by galactose isomerization by using arabinose isomerase, which includes the step of adding borate buffer, wherein the borate is added in an amount of 40 mol per 100 mol of galactose, and wherein the isomerization is performed in a pH range of 8.5 to 9 and a temperature range of 60° C. to 70° C.

2. The manufacturing method of tagatose according to claim 1, wherein the isomerization is performed at a temperature of 60° C.

* * * * *

UNITED STATES PATENT AND TRADEMARK OFFICE
CERTIFICATE OF CORRECTION

PATENT NO. : 8,481,720 B2  Page 1 of 1
APPLICATION NO. : 12/513866
DATED : July 9, 2013
INVENTOR(S) : Kim et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 692 days.

Signed and Sealed this
Eighth Day of September, 2015

Michelle K. Lee
*Director of the United States Patent and Trademark Office*